United States Patent [19]

Bergamaschi et al.

[11] Patent Number: 4,570,013
[45] Date of Patent: Feb. 11, 1986

[54] BIPHENYLYLALKANOIC ACID DERIVATIVES, METHODS OF PREPARATION AND PHARMACEUTICAL COMPOSITIONS THEREFROM

[75] Inventors: Mario Bergamaschi, Monza; Gian B. Gervasi, Arese; Vittorio Vecchietti; Massimo Signorini, both of Milan, all of Italy

[73] Assignee: Dr. L. Zambeletti S.p.A., MIlan, Italy

[21] Appl. No.: 668,650

[22] Filed: Nov. 6, 1984

[30] Foreign Application Priority Data

Nov. 28, 1983 [IT] Italy ............... 23912 A/83

[51] Int. Cl.$^4$ ........................... C07C 69/76
[52] U.S. Cl. ................... 560/102; 549/549
[58] Field of Search ............ 560/102; 514/532

[56] References Cited

FOREIGN PATENT DOCUMENTS 77720  9/1984  European Pat. Off. ............ 102/
1268008 10/1978 United Kingdom ............ 560/102

Primary Examiner—Paul J. Killos
Attorney, Agent, or Firm—Bucknam and Archer

[57] ABSTRACT

Novel compounds of formula

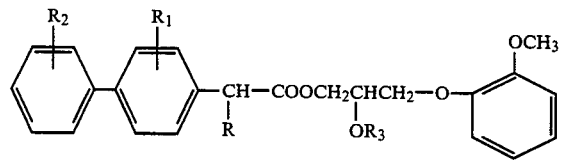

are described which have antipyretic, analgesic and antiinflammatory activity. R is hydrogen, $C_1$–$C_3$ linear or branched alkyl; $R_1$ and $R_2$ are hydrogen, halogen, unsubstituted or esterified hydroxy, alcoxy, and may be the same or different; $R_3$ is hydrogen, $C_1$–$C_4$ linear or branched aliphatic acyl, unsubstituted or substituted aroyl, alkylaroyl or hetaroyl groups.

9 Claims, No Drawings

BIPHENYLYLALKANOIC ACID DERIVATIVES, METHODS OF PREPARATION AND PHARMACEUTICAL COMPOSITIONS THEREFROM

The present invention relates to novel compounds of general formula I

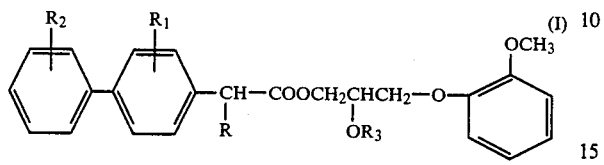

their method of preparation and pharamaceutical applications.

In general formula I, R is hydrogen or $C_1$–$C_3$ straight chain or branched alkyl; $R_1$ and $R_2$, which may be the same or different, are hydrogen, halogen, hydroxy, free or esterified, alcoxy; $R_3$ is hydrogen, $C_1$–$C_4$ linear or branched aliphatic acyl, unsubstituted or substituted aroyl, alkylaroyl or hetaroyl groups.

Biphenylylacetic acid ester endowed with antiinflammatory activity are known and described, for instance, in GB No. 1,268,008, JP No. 9033-244A and EP No. 77720; said esters are nevertheless structurally different from the compounds (I) which have the 3-(2-methoxyphenoxy)-propan-2-ol group. The same group is present in the compound claimed in BE No. 895,111 which differs substantially from those herein described, being a 2-(p-isobutyl)phenyl-propionic acid (ibuprofen) derivative.

The novel coumpounds according to the invention exhibit antipyretic, analgesic and antiinflammatory activity. They inhibit cyclooxygenase, blocking the synthesis of prostaglandins and thromboxane, as well as the platelet aggregation. The compounds according to formula I in which $R_3$ is hydrogen are synthesized according to known methods in which the compound of formula II 2-(2,3-epoxypropoxy)-1-methoxybenzene, reacts with a biphenylylalkanoic acid of formula III:

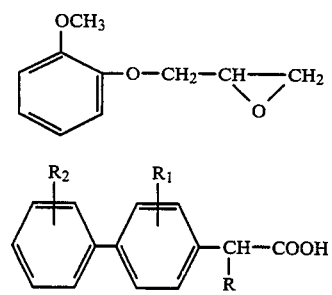

in the presence of a base for the purpose of generating the corresponding anion in a solvent which may be protic solvent such as an alcohol or water or an aprotic solvent which may be dioxane, tetrahydrofuran, etc.

Suitable bases for this purpose are inorganic substances such as KOH, NaOH, $Na_2CO_3$, $K_2CO_3$, CaO, etc., as well as organic bases such as trimethylamine, triethylamine, tetramethylguanidine, pyridine, lutidine, etc.

According to another method, the compounds of general formula I are prepared by reacting the compound of formula II with a salt of the biphenylylalkanoic of formula III in a suitable solvent. These solvents may be water, alcohol, ketones, dioxane, tetrahydrofuran, dimethylformamide, dimethylsulfoxide, etc. In addition the compounds of formula I may be prepared by reacting guaiacol of formula IV with epichlorohydrin of formula V in the presence of an organic base such as piperidine or pyrrolidine as a catalyst to obtain the compound of formula VI, 2-(3-chloro-2-hydroxypropoxy)-methoxybenzene, according to the reaction scheme hereinbelow:

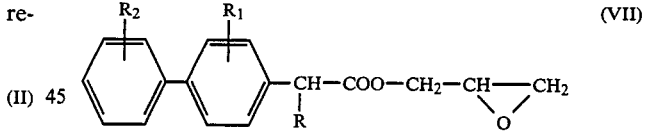

The latter compound of formula VI, when it reacts with a salt of the desired biphenylylalkanoic acid in a suitable solvent, leads to the desired compound of formula I. For this reaction, suitable solvents are protic substances such as alcohols, as well as aprotic substances such as dioxane, tetrahydrofuran, dimethylformamide, acetone, etc.

The compounds of formula I are also prepared by reacting a salt of the desired biphenylylalkanoic acid with epichlorohydrin so as to obtain the epoxy esters of formula VII:

$$R_2 \quad R_1 \qquad (VII)$$

[structure: biphenyl–CH(R)–COO–CH$_2$–CH—CH$_2$ (epoxide)]

The latter compounds by reaction with sodium or potassium guaiacolate in alcohols or tetrahydrofuran or dioxane give the compounds of formula I. For all these reactions mentioned hereinabove, the optimum temperature range is between 25° C. and the boiling point of the solvent being used.

With respect to the derivatives of formula I in which $R_3$ is an acyl group, the latter are synthesized by esterifying the corresponding compound I of formula I in which $R_3$ is hydrogen according to well known esterification methods with an alcohol, such as, for instance, the reaction of the compound of formula I in which $R_3$ is hydrogen with an acylchloride in the presence of a base such as pyridine or triethylamine, etc. or with an anhydride or a mixed anhydride.

PHARMACOLOGY

The novel compounds of formula I exhibit antipyretic, analgesic, antiinflammatory properties; they exhibit antiaggregating activity and the ability of inhibiting cyclooxygenase. These properties are particularly significant in the case of the compound of formula Ia hereinbelow, 1-biphenylylacetoxy-3-(2-methoxyphenoxy)-propan-2-ol:

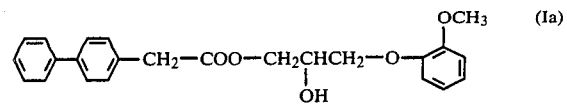

The antiinflammatory activity has been studied utilizing the method of Winter (C. A. Winter, Proc. Soc. Exptl. Biol. Med., 11, 544 (1962)), determining the ability of the compounds being examined to antagonize the formation of an oedema induced in the rats' paw by intradermic injection of carrageenin. Under these experimental conditions, the compound of formula Ia has exhibited interesting antiedemigenic activity with an effective dose $ED_{50}=22.5$ mg/kg$^{-1}$ orally.

The analgesic activity has been studied according to the method described by Siegmund (E. Siegmund et al, Proc. Soc. Exptl. Biol. Med., 95, 729 (1957)), according to which the algogenic stimulus consists of the intraperitoneal injection of 2-phenylparabenzoquinone and the algesia manifests itself in repeated abdominal contractions with an extension of the rear limbs and contorsions of the body ("writhing test").

The test is carried out with Swiss mice of 25 g average weight and the compound of formula Ia has shown to have a significant analgesic activity ($ED_{50}=32$ mg/kg$^{-1}$ orally), whose onset is very precocious (15 minutes after administration of the substance) as shown by the data in Table 1 hereinbelow which shows the analgesic action, (writhings caused by 2-phenylparabenzoquinone in mice) for compound Ia and for biphenylylacetic acid in the respective doses of 32 mg/kg$^{-1}$ orally and 12 mg/kg$^{-1}$ orally, which correspond to the $ED_{50}$ of the two substances. The compound of formula Ia is devoid of central analgesic activity; indeed it has not shown any protective activity in the hot plate test up to the dose of 200 mg/kg$^{-1}$ orally in mice.

TABLE I

| No. | Substance | mg/Kg orally | 5 minutes No. Contorsions | % | 15 minutes No. Contorsions | % | 30 minutes No. Contorsions | % | 1 hour No. Contorsions | % |
|---|---|---|---|---|---|---|---|---|---|---|
| 10 | Controls | — | 45.7 ± 4.1 | — | 52.2 ± 4.2 | — | 49.0 ± 3.2 | — | 50.3 ± 3.2 | — |
| 10 | Biphenylylacetic acid | 12 ($ED_{50}$) | 33.4 ± 3.0 | −27 | 31.0 ± 4.7 | −41 | 21.3 ± 2.6 | −57 | 25.6 ± 2.9 | −49 |
| 10 | Compound Ia | 32 ($ED_{50}$) | 33.1 ± 4.1 | −28 | 35.1 ± 3.4 | −33 | 22.7 ± 2.4 | −54 | 26.8 ± 3.3 | −47 |

| No. | Substance | mg/Kg orally | 2 hours No. Contorsions | % | 3 hours No. Contorsions | % | 4 hours No. Contorsions | % | 5 hours No. Contorsions | % |
|---|---|---|---|---|---|---|---|---|---|---|
| 10 | Controls | — | 46.9 ± 2.2 | — | 49.0 ± 4.4 | — | 48.7 ± 3.4 | — | 50.7 ± 2.3 | −1 |
| 10 | Biphenylylacetic acid | 12 ($ED_{50}$) | 25.1 ± 2.8 | −42 | 26.0 ± 4.0 | −47 | 34.9 ± 3.6 | −28 | 45.0 ± 2.3 | −1 |
| 10 | Compound Ia | 32 ($ED_{50}$) | 25.4 ± 3.8 | −46 | 27.6 ± 3.4 | −44 | 33.5 ± 3.6 | −31 | 45.0 ± 3.2 | −1 |

Method according to Siegmund

The antipyretic activity has been studied according to the method of C. Winter, Toxicol. and Appl. Pharmacol., 5, 247 (1963), in rats, by determining the ability of the substance to reduce the increase of body temperature caused by the subcutaneous administration of brewer's yeast. Under these experimental conditions, compound Ia has shown a remarkable antipyretic activity with $ED_{50}$ of 14 mg/kg$^{-1}$ orally. The values reported in Table II show in addition that the antipyretic activity of compound Ia manifests itself within one hour after the treatment and continues after the sixth hour.

TABLE II

| | | | | | | | | | | | |
|---|---|---|---|---|---|---|---|---|---|---|---|
| | | | | | Hyperthermia caused by brewer's yeast in rats | | | | | | |
| No | COMPOUND | mg/kg/os | Normal base temp. | Temp. after yeast | Temp. Increase | Temperature after administration of the substance after: | | | | | |
| | | | | | | 1 h t° C. | Δt° C. | 2 h t° C. | Δt° C. | 3 h t° C. | P/S* | Δt° C. |
| 10 | Normal Controls | — | 37.20±0.08 | 37.31±0.06 | +0.11 | 37.31±0.05 | +0.0 | 37.21±0.05 | −0.10 | 37.17±0.05 | — | −0.14 |
| 10 | Hyperthermic Controls | — | 37.14±0.08 | 38.41±0.07 | +1.27 | 38.64±0.09 | +1.33 | 38.46±0.09 | +1.25 | 38.39±0.08 | — | +1.22 |
| 10 | Biphenylylacetic acid | 3 | 37.18±0.07 | 38.48±0.10 | +1.30 | 38.16±0.07 | −0.48 | 37.81±0.05 | −0.65 | 37.69±0.08 | 2/10 | −0.70 |
| 10 | Biphenylylacetic acid | 6 | 37.21±0.06 | 38.48±0.10 | +1.27 | 37.80±0.09 | −0.84 | 37.46±0.09 | −1.00 | 37.28±0.07 | 5/10 | −1.11 |
| 10 | Biphenylylacetic acid | 12 | 37.33±0.07 | 38.59±0.08 | +1.26 | 37.71±0.08 | −0.93 | 37.33±0.06 | −1.13 | 37.09±0.07 | 8/10 | −1.30 |
| 10 | Compound (Ia) | 6 | 37.17±0.06 | 38.41±0.08 | +1.24 | 38.01±0.07 | −0.63 | 37.71±0.09 | −0.75 | 37.70±0.102 | 1/10 | −0.69 |
| 10 | Compound (Ia) | 12 | 37.23±0.05 | 38.47±0.05 | +1.24 | 37.81±0.06 | −0.83 | 37.40±0.05 | −1.06 | 37.32±0.08 | 4/10 | −1.07 |
| 10 | Compound (Ia) | 24 | 37.20±0.07 | 38.47±0.05 | +1.28 | 37.66±0.05 | −0.98 | 37.31±0.05 | −1.15 | 37.13±0.06 | 8/10 | −1.26 |
| No. | COMPOUND | mg/kg/os | Normal base temp. | Temp. after yeast | Temp. Increase | Temperature after administration of the substance after: | | | | | |
| | | | | | | 4 h t° C. | Δt° C. | 5 h t° C. | Δt° C. | 6 h t° C. | Δt° C. |
| 10 | Normal Controls | — | 37.20±0.08 | 37.31±0.06 | +0.11 | 37.19±0.05 | −0.12 | 37.18±0.07 | −0.13 | 37.21±0.04 | −0.10 |

TABLE II-continued

| | | | Hyperthermia caused by brewer's yeast in rats | | | | | | | |
|---|---|---|---|---|---|---|---|---|---|---|
| 10 | Hyperthermic Controls | — | 37.14±0.08 | 38.41±0.07 | +1.27 | 38.30±0.08 | +1.11 | 38.26±0.09 | +1.08 | 38.24±0.102 | +1.03 |
| 10 | Biphenylylacetic acid | 3 | 37.18±0.07 | 38.48±0.10 | +1.30 | 37.89±0.08 | −0.41 | 38.12±0.13 | −0.14 | 38.19±0.11 | −0.05 |
| 10 | Biphenylylacetic acid | 6 | 37.21±0.06 | 38.48±0.10 | +1.27 | 37.40±0.09 | −0.90 | 37.65±0.10 | −0.63 | 37.81±0.12 | −0.37 |
| 10 | Biphenylylacetic acid | 12 | 37.33±0.07 | 38.59±0.08 | +1.26 | 37.18±0.07 | −1.12 | 37.43±0.08 | −0.93 | 37.58±0.105 | −0.66 |
| 10 | Compound (Ia) | 6 | 37.17±0.06 | 38.41±0.08 | +1.24 | 37.85±0.14 | −0.45 | 38.07±0.15 | −0.19 | 38.10±0.101 | −0.14 |
| 10 | Compound (Ia) | 12 | 37.23±0.05 | 38.47±0.05 | +1.24 | 37.41±0.07 | −0.89 | 37.66±0.09 | −0.50 | 37.88±0.07 | −0.36 |
| 10 | Compound (Ia) | 24 | 37.20±0.07 | 38.47±0.05 | +1.28 | 37.16±0.06 | −1.14 | 37.34±0.05 | −0.92 | 37.55±0.06 | −0.69 |

*Ratio of protected animals with respect to total screened animals.
Method according to C. Winter et al.

The gastrolesive action has been studied in rats after administration of single doses of compound Ia and the results so obtained on the basis of the experimental tests show that the substance is capable of producing lesions in the gastric mucosa only in doses 2–4 times greater than the useful therapeutic dose.

Table III summarizes the data of antiinflammatory, analgesic, antipyretic and gastrolesive activity of the compound Ia compared with the corresponding values for biphenylylacetic acid, N-2-pyridinyl-(1,1'-biphenyl)-4-acetamide (diphenpyramide) and 6-methoxy-α-methyl-2-naphthaleneacetic acid (naproxen).

The activity of compound Ia on the metabolism of arachidonic acid has been studied in virto according to the method described by B. Fjalland, J. Pharm. Pharmacol., 26, 448 (1974). In these tests the compound being examined is capable of inhibiting the synthesis of prostaglandin and thromboxane caused by arachidonic acid (AA) incubated with lung tissue of guinea pigs ($IC_{50}=0.05$ mM). The activity on the platelet aggregation induced by arachidonic acid has been determined in vitro on plasma enriched with platelets of guinea pigs according to the method described by G. V. R. Born, Nature 194, 927 (1962). The anti aggregating activity of compound Ia results to be proportional to the concentration used, with $IC_{50}=123$ mM.

The ex vivo study in guinea pigs in addition has shown that the oral administration of a dose equal to the antiinflammatory $ED_{50}$, causes a decrease in the aggregating action of arachidonic acid which starts three hours after the administration and remains up to the fifth hour.

TOXICITY

Compound Ia has not shown any mutagenic action according to the Ames test carried out on the following species of Salmonella thyphimurium: TA 1535; TA 1538; TA 100; TA 98, in the absence and in the presence of metabolic activation up to a concentration of 5000 μg per plate.

Finally, the following values of DL50 have been determined in mice for compound Ia:
$DL_{50}$ orally $=3330$ mg/kg$^{-1}$
$DL_{50}$ ip $=260$ mg/kg$^{-1}$.

The following examples are submitted for the purpose of further illustration of the invention, without limiting in any way the scope thereof.

EXAMPLE 1

1-Biphenylylacetoxy-3-(2-methoxyphenoxy)-propan-2-ol (Compound Ia)

A suspension of 20 g of 2-(2,3-epoxypropoxy)-1-methoxybenzene, 70 g of biphenylylacetic acid, 100 cc of 1N sodium hydroxide, is kept under reflux for one hour. After cooling to room temperature, the suspension is extracted three times with 75 cc each of ether. The combined ether extracts are then washed with 8% sodium carbonate and then water up to neutrality. After drying and evaporation of the solvent under vacuum, a dense oil is obtained which solidifies after stirring a few hours with diisopropyl ether. The product is recrystallized from diethyl ether/diisopropyl ether in a ratio of 1:1.

Yield: 37 g (85%); m.p.: 70° C.;
Empirical formula: $C_{24}H_{24}O_5$
Molecular weight: 392.43

The elementary analysis, infrared and NMR spectra confirmed the structure.

According to the same method starting from 2-(2,3-epoxypropoxy)-1-methoxybenzene and from the corresponding biphenylylalkanoic acids, the following compounds are obtained:

TABLE III

| | PHARMACOLOGICAL ACTIVITY | | | |
|---|---|---|---|---|
| COMPOUND | Antiinflammatory activity (oedema caused by carrageenin in rats) $ED_{50}$mg · kg$^{-1}$ os | Analgesic activity (against pain caused by 2-phenyl-p-benzo-quinone in mice) $ED_{50}$mg · kg$^{-1}$ os | Antipyretic activity (temperature increase caused by brewer's yeast, in rats) $ED_{50}$mg · kg$^{-1}$ os | Gastrolesive activity in rats $ED_{50}$mg · kg$^{-1}$ os |
| Compound (Ia) Mol. Wt.: 392.4 | 22.5 | 32.0 | 14.0 | 61.7 |
| Biphenylylacetic acid Mol. Wt.: 212.2 | 10.9 | 12.0 | 6.0 | 16.5 |
| Diphenpyramide Mol. Wt.: 288.3 | 19.9 | 97.0 | 22.5 | 76.0 |
| Naproxen Mol. Wt.: 230.3 | 24 | 20 | 112 | 17 |

1-[2-(biphenylyl)propionyloxy]-3-(2-methoxyphenoxy)-propan-2-ol;
1-(4″-fluorobiphenylylacetoxy)-3-(2-methoxyphennoxy)-propan-2-ol;
1-(4″-methoxybiphenylylacetoxy)-3-(2-methoxyphenoxy)-propan-2-ol;
1-(2′-chlorobiphenylylacetoxy)-3-(2-methoxyphennoxy)-propan-2-ol.

EXAMPLE 2

1-Biphenylylacetoxy-3-(2-methoxyphenoxy)propan-2-ol formylester (Compound Ib)

To 50 cc of mixed formic-acetic anhydride cooled to 0° C. are added 11.7 g of 1-biphenylylacetoxy-3-(2-methoxyphenoxy)-propan-2-ol (Compound Ia) and 10 cc of pyridine. The mixture is allowed to stand one hour at 0° C. and then three hours at room temperature. The solution is evaporated to dryness, the residue is dissolved in methylene chloride, the solution is washed with dilute hydrochloric acid and then with saturated sodium bicarbonate and finally with water up to neutrality. The solution is dried over sodium sulfate, evaporated to dryness and the solid residue is recrystallized from diisopropyl ether.

M.p.: 90° C.
Yield: 11.4 g (91%)
Empirical formula: $C_{25}H_{24}O_6$

The elementary analysis, infrared and NMR spectra confirmed the structure.

EXAMPLE 3

1-Biphenylylacetoxy-3-(2-methoxyphenoxy)-propan-2-ol benzoylester (Compound Ic)

To a solution of 3.2 g of 1-biphenylylacetoxy-3-(2-methoxyphenoxy)-propan-2-ol (Compound Ia) in 10 cc of pyridine is added 3 cc of benzoylchloride. After a few hours at room temperature under stirring, the solution is evaporated to dryness. The residue is dissolved in chloroform and the solution is washed with dilute hydrochloric acid, then sodium bicarbonate and finally water up to neutrality. The solution is dried on sodium sulfate and evaporated to dryness. The residual solid is washed with a small amount of diethyl ether and then it is recrystallized with diisopropyl ether.

Yield: 3.47 g (86%)
m.p.: 80° C.
Empirical formula: $C_{31}H_{28}O_6$
Molecular weight: 496.53

The elementary analysis, infrared and NMR spectra confirmed the structure.

The following compounds are obtained according to the same method by esterification of 1-biphenylylacetoxy -3-(2-methoxyphenoxy)-propan-2-ol with the corresponding acylchloride:
1-biphenylylacetoxy-3-(2-methoxyphenoxy)-propan-2-ol nicotinoylester;
1-biphenylylacetoxy-3-(2-methoxyphenoxy)-propan-2-ol p-chlorobenzoylester;
1-biphenylylacetoxy-3-(2-methoxyphenoxy)-propan-2-ol 2- or 3-thenoylester;
1-biphenylylacetoxy-3-(2-methoxyphenoxy)-propan-2-ol phenylacetylester;
1-biphenylylacetoxy-3-(2-methoxyphenoxy)-propan-2-ol isobutyroylester.

THERAPEUTICAL APPLICATIONS

In view of the high degree of tolerability and the pharmacological properties, the compounds according to the present invention may be used in human or animal therapy as antipyretic, analgesic and antiinflammatory agents. The present invention also covers all the industrial aspects connected with the use of the compounds of formula I as therapeutical agents. An essential aspect of the invention, therefore, resides in providing pharmaceutical compositions which contain as the active ingredient a predetermined and therapeutical effective amount of at least one compound of formula I. The compositions according to the present invention may be provided in the form of sugar-coated tablets, tablets, capsules, syrups, suppositories, etc.

Pharmaceutical compositions containing the active ingredients may be administered by the oral route or the rectal route and the amount per unit dose is in general between 25 and 200 mg. The formulations in addition may also contain other active substances provided they are pharmaceutically acceptable and compatible and in addition, the excipients conventionally used in the pharmaceutical industry. The following examples further illustrate the invention:

| | |
|---|---|
| (a) Tablets | |
| 1-Biphenylylacetoxy-3-(2-methoxyphenoxy)-propan-2-ol (Compound Ia) | 200 mg |
| Excipients (starch, lactose, Mg stearate, wetting agent, binding agent) q.s. | 450 mg |
| (b) Hard gelatin capsules | |
| Compound (Ia) | 100 mg |
| Excipients (lactose, Mg stearate, wetting agent) q.s. | 300 mg |
| (c) Soft gelatin capsules | |
| Compound (Ia) | 150 mg |
| Vegetable oil q.s. | 300 mg |
| (d) Soft gelatin capsules | |
| Compound (Ia) | 100 mg |
| Vegetable oil q.s. | 350 mg |
| (e) Oral suspension | |
| Compound (Ia) | 5 g |
| Excipients (cellulose, sodium carboxymethylcellulose, non-ionic surface active agent, saccharose, xylitol, preservative, aromatizing agent, water) q.s. | 100 cc |
| (f) Suppositories for adults | |
| Compound (Ia) | 100 mg |
| Mixture of semisynthetic triglycerides q.s. | 2 g |
| (g) Suppositories for children | |
| Compound (Ia) | 50 mg |
| Mixture of semisynthetic triglycerides q.s. | 1 g |

We claim:
1. A compound of general formula I

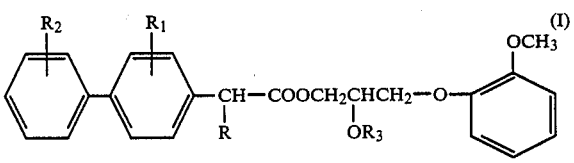

wherein
R is hydrogen, $C_1$–$C_3$ linear or branched alkyl;

$R_1$ and $R_2$, which may be the same or different, are hydrogen, halogen, unsubstituted or esterified hydroxy, alcoxy;

$R_3$ is hydrogen, $C_1$–$C_4$ linear or branched aliphatic acyl, unsubstituted or substituted aroyl, alkyl aroyl or hetaroyl groups.

2. A compound according to claim 1 wherein R is hydrogen or methyl, $R_1$ is hydrogen or 2'-Cl, $R_2$ is hydrogen, 4''-F or 4''-OCH$_3$ and $R_3$ is selected in the group consisting of formyl, benzoyl, nicotinoyl, p-chlorobenzoyl, 2-thenoyl, 3-thenoyl, phenylacetyl or isobutyroyl groups.

3. 1-Biphenylylacetoxy-3-(2-methoxyphenoxy)-propan-2-ol.

4. A process for preparation of the compound of formula I according to claim 1 wherein $R_3$=H, which consists of reacting a biphenylylalkanoic acid of formula III

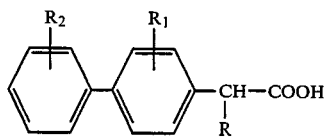 (III)

wherein $R_2$, $R_3$ and R are the same as hereinabove with 2-(2,3-epoxypropoxy)-1-methoxybenzene in the presence of a base.

5. The process according to claim 4 wherein said base is an inorganic base which is a member selected from the group consisting of KOH, NaOH, Na$_2$CO$_3$, K$_2$CO$_3$, CaO.

6. The process according to claim 4 wherein the base is an organic base which is a member selected from the group consisting of trimethylamine, triethylamine, tetramethylguanidine, pyridine, lutidine.

7. The process of preparation of a compound of formula I according to claim 1 wherein $R_3$ is acyl, which consists of reacting a compound of general formula I wherein $R_3$ is hydrogen with an acyl chloride or mixed anhydride in the presence of a base.

8. A pharmaceutical composition in unit dose form having antipyretic, analgesic and antiinflammatory activity which contains as the active ingredient an effective amount per unit dose of a compound of general formula I according to claim 1 and at least one inert excipient.

9. A pharmaceutical composition according to claim 8 wherein said compound of formula I is 1-biphenylylacetoxy-3-(2-methoxyphenoxy)-propane-2-ol.

* * * * *